United States Patent [19]

Chikama

[11] 4,190,041
[45] Feb. 26, 1980

[54] CLEANING DEVICE FOR WIRE GUIDE TUBE IN AN ENDOSCOPE

[75] Inventor: Toshio Chikama, Tokyo, Japan

[73] Assignee: Machida Endoscope Co., Ltd., Tokyo, Japan

[21] Appl. No.: 832,338

[22] Filed: Sep. 12, 1977

[51] Int. Cl.² .............................................. A61B 1/00
[52] U.S. Cl. ............................................. 128/4; 128/6
[58] Field of Search ............................... 128/4–9, 128/303.15

[56] References Cited

U.S. PATENT DOCUMENTS

| | | | |
|---|---|---|---|
| 1,345,406 | 7/1920 | Rimmer | 128/7 |
| 1,627,941 | 5/1927 | Wappler | 128/7 |
| 2,002,595 | 5/1935 | Wappler | 128/7 |
| 2,227,727 | 1/1941 | Leggiadro | 128/6 |
| 2,516,494 | 7/1950 | Wallace | 128/5 |
| 3,149,633 | 9/1964 | Zingale | 128/303.15 |
| 3,830,225 | 8/1974 | Shinnick | 128/4 X |

FOREIGN PATENT DOCUMENTS 932574 9/1955 Fed. Rep. of Germany ............ 128/7

Primary Examiner—Clifford D. Crowder
Assistant Examiner—Steven A. Bratlie
Attorney, Agent, or Firm—Peter L. Berger

[57] ABSTRACT

The present invention relates to a side view type or a direct view type endoscope which is used not only for examining the inner portion of stomachs and bowels, but also for cutting out or treating polyps on the wall of stomachs and bowels by an extractor which is inserted through an extractor leading tube of the endoscope. In said endoscope, the rear end portion of a wire guide tube of the extractor operating device is opened or can be opened for washing and sterilization of said wire guide tube.

9 Claims, 11 Drawing Figures

CLEANING DEVICE FOR WIRE GUIDE TUBE IN AN ENDOSCOPE

BACKGROUND OF THE INVENTION

The present invention relates to an endoscope, or more particularly, to a wire guide tube of the extractor operating device in an endoscope.

A side view type or a direct view type endoscope which is used for examining the inner portion of the stomach and bowels or used for cutting out or treating polyps on the wall of the stomach and bowels by an extractor which is inserted through an extractor leading tube must be, nowadays, thoroughly washed and sterilized after using it. The washing and sterilization must be done not only on the surface of the endoscope, but also on the inner portion of the tubes in the endoscope. A tube which is opened at both its ends such as an extractor leading tube or a water and air supplying tube can be thoroughly washed and sterilized by the circulation of cleanser and disinfectant. But the rear end portion of the wire guide tube of the extractor operating device is closed and connected to the extractor operating device, and sufficient washing and sterilization of pflegm or body fluid which flows into the wire guide tube is difficult.

SUMMARY OF THE INVENTION

The present invention aims at perfect washing and sterilization of the wire guide tube of the extractor operating device in an endoscope. This is achieved by making said wire guide tube open at both its ends with the aid of a through tube which extends to the outside of a handle at the coupling of the extractor operating device or at the rear end of said wire guide tube. Additionally, this may be achieved by connecting said wire guide tube with a water and air supplying tube whose both ends are open, or by providing a piston mechanism at the rear end of said wire guide tube, thus enabling cleanser and disinfectant to circulate through said wire guide tube.

The first object of the present invention is to wash and sterilize the wire guide tube perfectly by making said wire guide tube open at both its ends with the aid of the through tube, which extends to the outside at the rear end of said wire guide tube or at the coupling of the extractor operating device.

The second object of the present invention is to get perfect washing and sterilization of the wire guide tube by connecting said wire guide tube with the tube whose both ends are opened such as the water and air supplying tube at the rear end of said wire guide tube or at the extractor operating device.

The third object of the present invention is to get perfect washing and sterilization of the wire guide tube by making both ends of said wire guide tube open through utilizing a water and air supplying tube as the wire guide tube at the same time.

The fourth object of the present invention is to get perfect washing and sterilization of the wire guide tube by a piston mechanism which is provided at the coupling of the extractor operating device situated at the rear end of said wire guide tube. The piston mechanism supplies the desired amount of cleanser and disinfectant when needed.

DETAILED DESCRIPTION OF THE PREFERRED EMBODIMENTS

Figure 1:
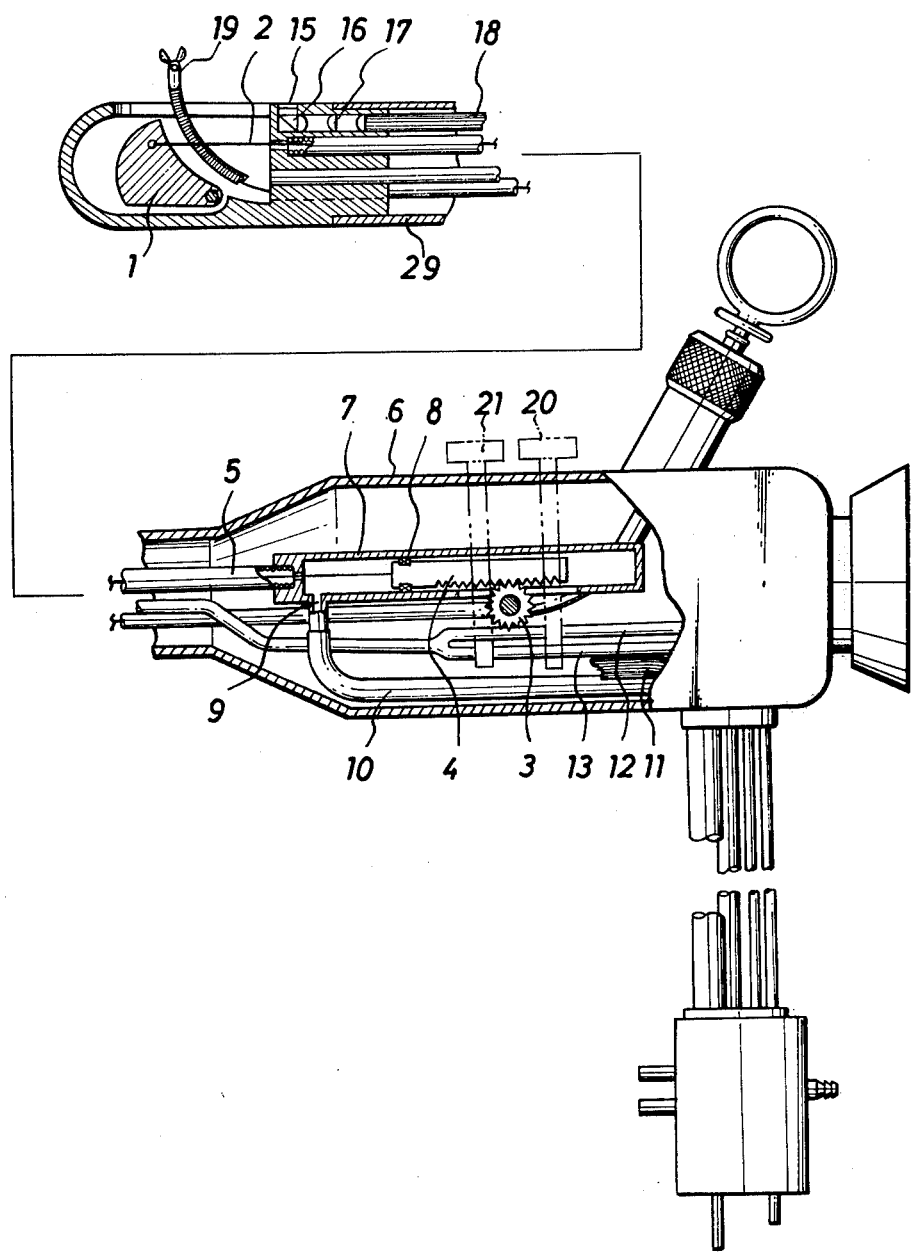
FIG. 1 is a partial sectional view of an embodiment in which a through tube is connected to a hollow portion which is connected with a wire guide tube of a extractor operating device.
Figure 2:
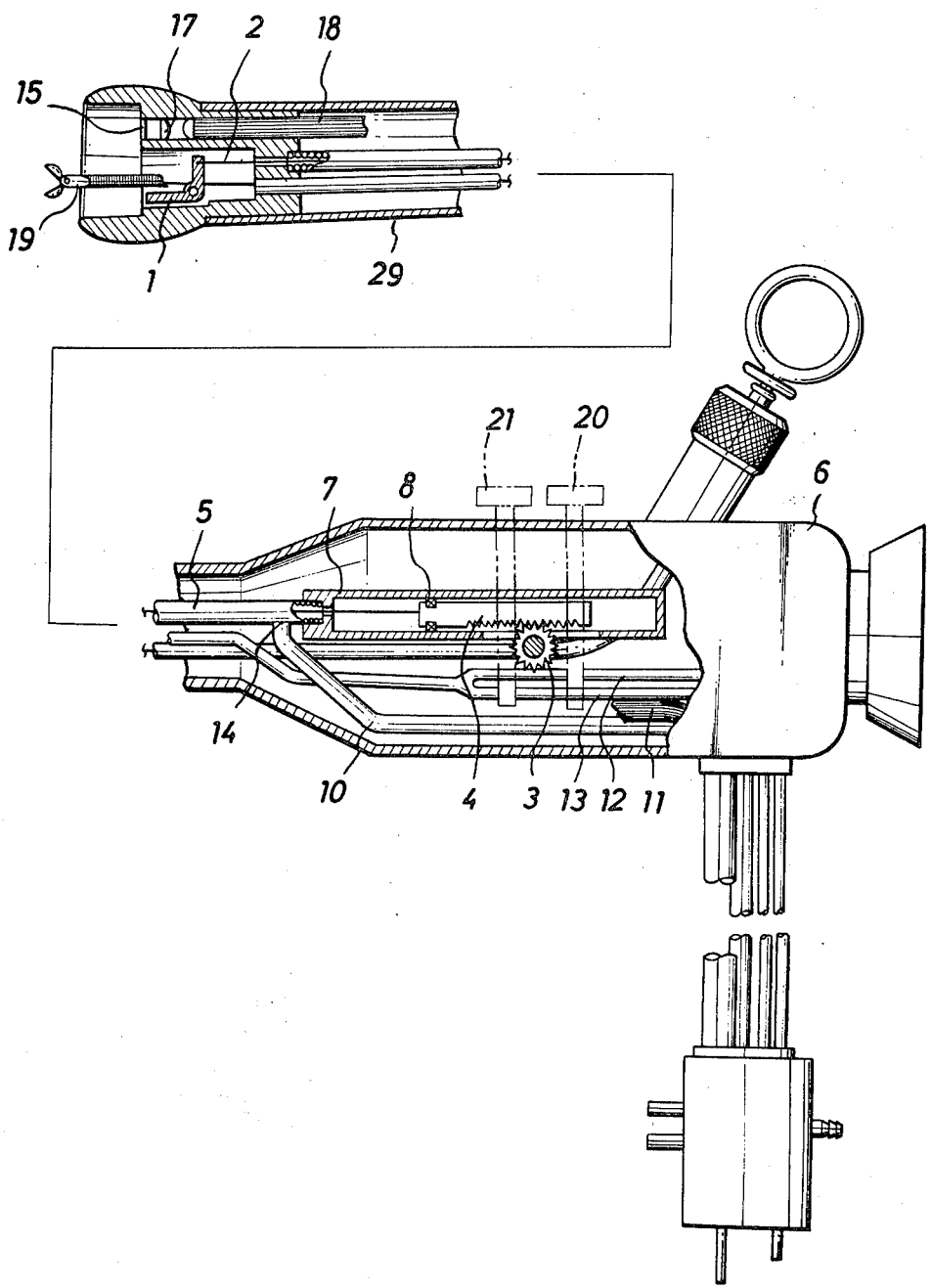
FIG. 2 is a partial sectional view of an embodiment in which a through tube is connected to the rear end portion of a wire guide tube of a extractor operating device.

FIG. 1 shows an embodiment of an operating device in an endoscope. A rack 4 is displaced by rotating a pinion 3 by a knob (not shown) situated outside of a handle, and said pinion 3 is connected to an extractor operating wire 2 which is connected to an extractor operating device 1. The end portion of a wire guide tube 5 in handle 6 is connected to a hollow portion 7. A packing 8 is provided in said hollow portion 7, and said rack 4 can be displaced in the horizontal direction by said pinion 3. An opening 9 is provided at the forward part of said rack 4 in said hollow portion 7. One end of a through tube 10 is connected to said opening 9, and said through tube 10 is tied up in a bundle with a light conducting fiber 11, an air supplying tube 12, a water supplying tube 13 and other wires. Said through tube 10 extends outside of a handle 6, and the forward end of said through tube 10 can be opened or shut at will. In FIG. 2, the before-mentioned through tube 10 is connected to an opening 14 situated at the rearward end of a wire guide tube 5, not to said hollow portion 7. The embodiment shown in FIG. 1 represents the top of a side view type endoscope, and the number 15 indicates an observation window, and the light is transmitted into an image tube 18 through a prism 16 and a lens 17. The number 19 indicates an extractor, the number 20 a valve of an air supplying tube 12, the number 21 a valve of a water supplying tube 13.

FIG. 2 shows an embodiment of the top of a direct view type endoscope. The number 1 indicates an exractor operating device which is actuated by an operating wire 2. The operating device of said operating wire 2 in handle 6 is composed of the before-mentioned rack 4 and pinion 3 system, but the device may be composed of a roller system (not shown) which is so made that the rear end of the operating wire is bound around the roller, and by rotating the roller, the wire is actuated. By these embodiments shown in FIGS. 1 and 2, the wire guide tube 5 is opened at its both ends with the aid of the through tube 10, thus resulting in perfect washing and sterilization with the cleanser and disinfectant which circulate in said wire guide tube 5.

Figure 3:
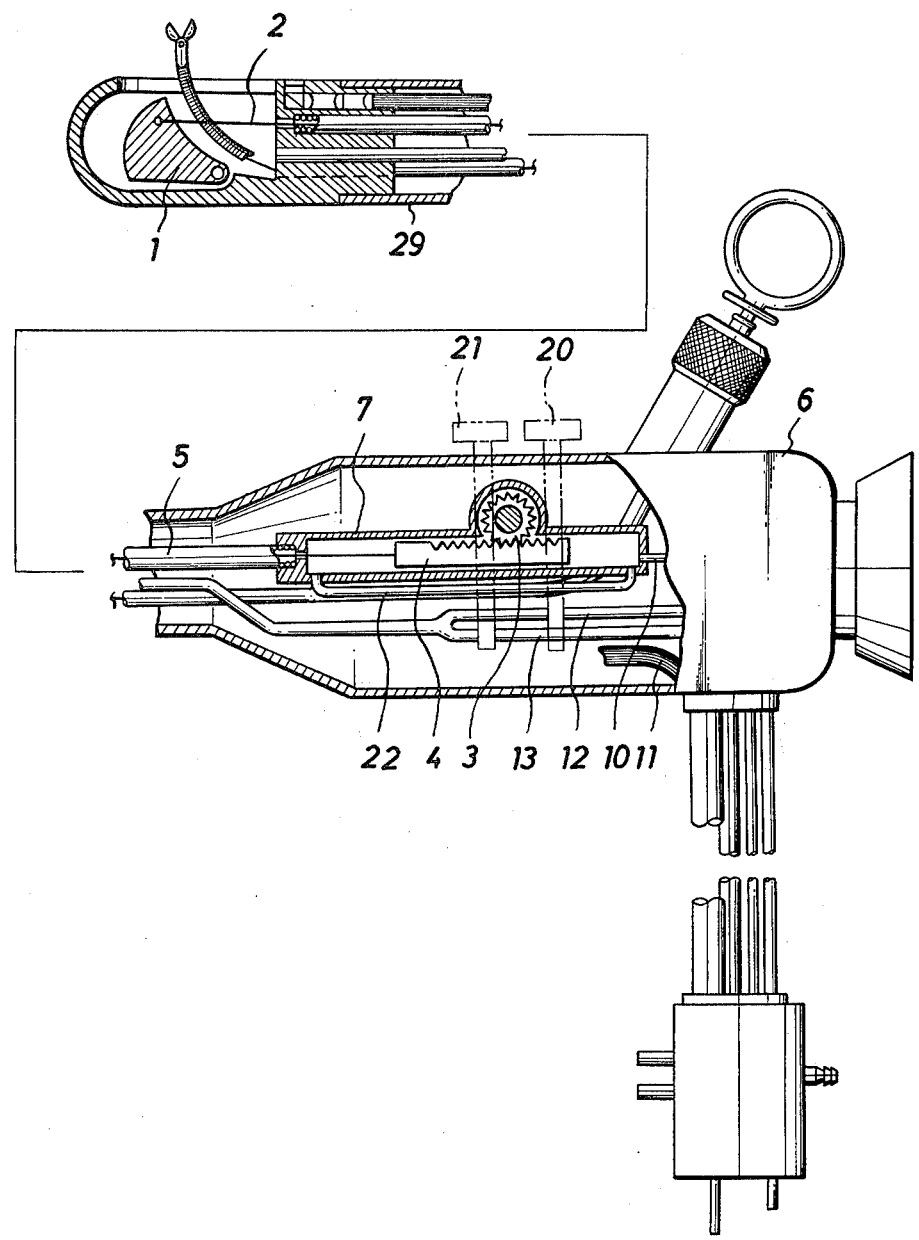
FIGS. 3a, 3b, 3c, 3d are partial sectional views of embodiments in which the by-passes are provided in the hollow portion.
Figure 3:
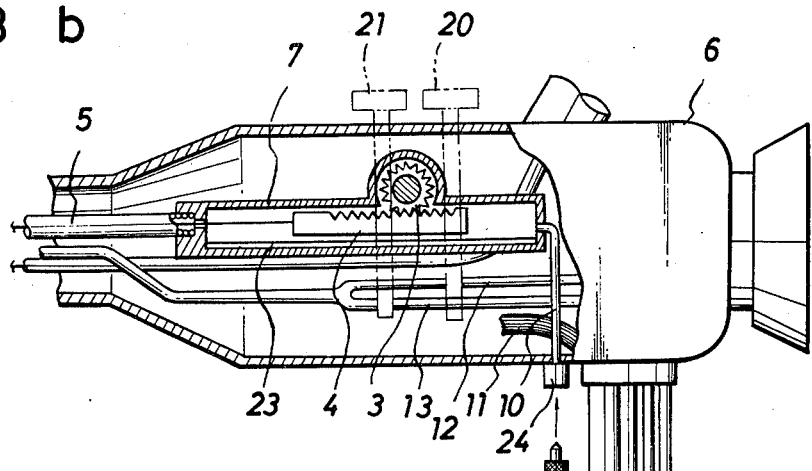
Figure 3:
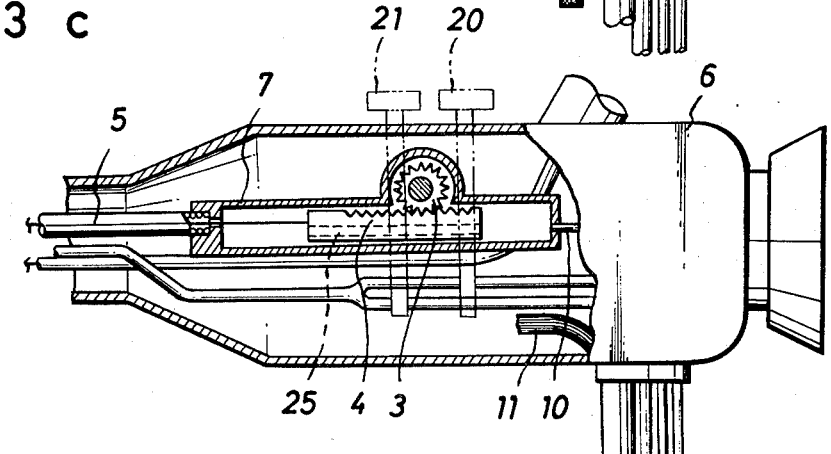
Figure 3:
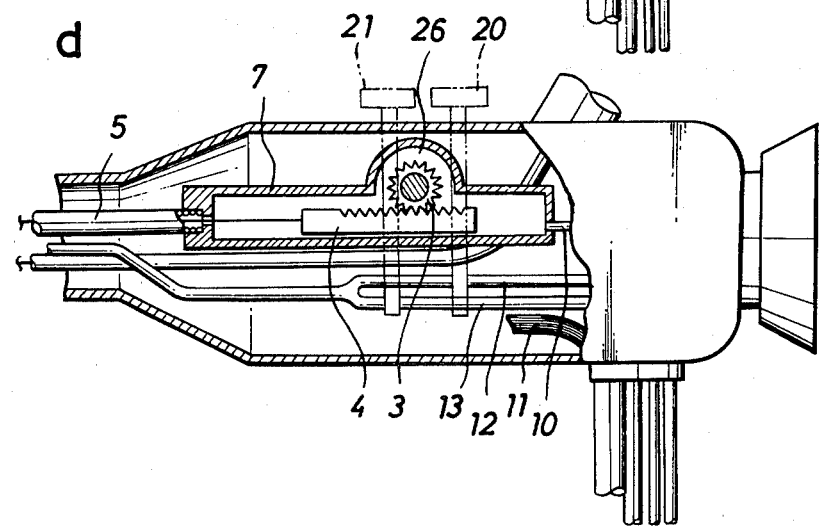

Another embodiment is shown in FIG. 3a. A by-pass 22 is provided to connect the forward end and the rear end of the hollow portion 7, and a rack 4 is provided between them. A through tube 10 is connected to the rear end portion of said hollow portion 7.

Another embodiment of the before-mentioned by-pass is shown in FIG. 3b. A gap 23 is provided between the rack 4 and the hollow portion 7, and said gap 23 is utilized as a by-pass. Said through tube 10 protrudes out of a handle 6, and a protruded opening 24 can be opened or shut at will.

FIG. 3c shows other embodiment of a by-pass. A through hole 25 is provided through the rack 4 in the hollow portion 7.

FIG. 3d shows other embodiment of a by-pass. A passage 26 is provided between the pinion 3 and the hollow portion 7.

By these embodiments shown in FIGS. 3a, 3b, 3c, 3d, the wire guide tube 5 is opened at its both ends like as the before-mentioned embodiments.

Figure 4:
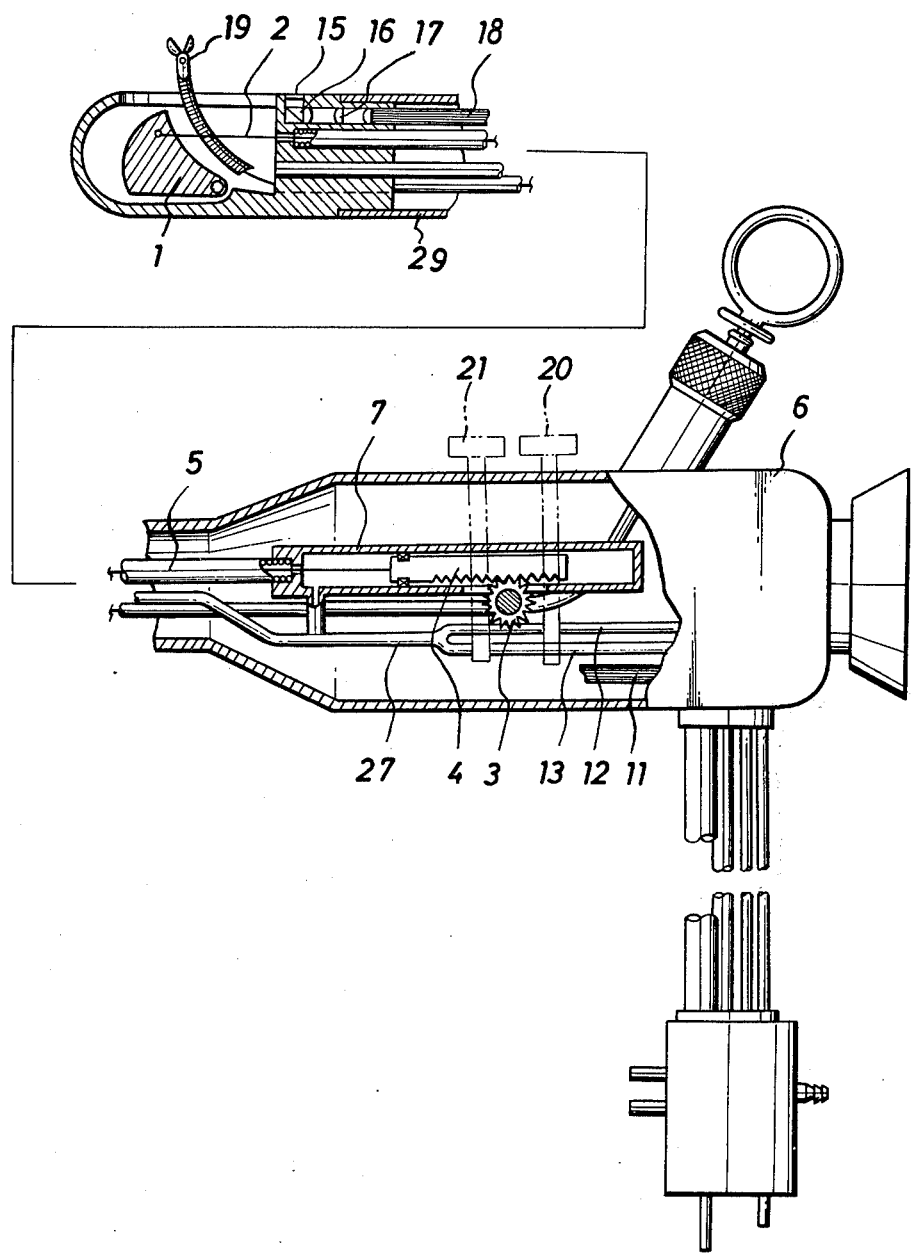
FIG. 4a is a partial sectional view of an embodiment in which a hollow portion is connected to the tube such as a water and air supplying tube whose both ends are opened.
FIG. 4b is a partial sectional view of an embodiment in which a hollow portion is connected to an extractor leading tube.
Figure 4:
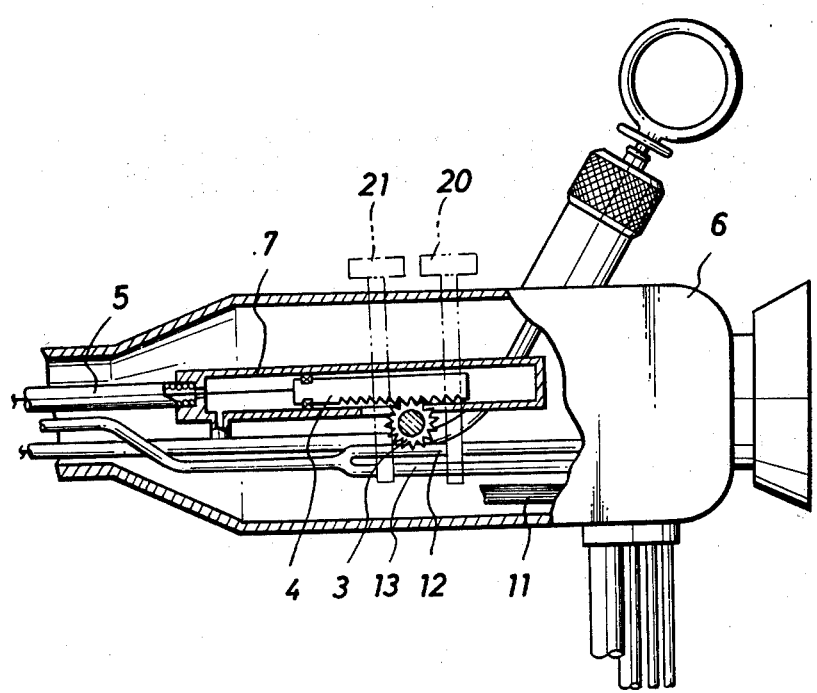

Another embodiment is shown in FIG. 4a in which the tube opened at its both ends such as a water and air supplying tube 27 is utilized instead of the through tube. The opening which is provided at the forward end of the hollow portion 7 or at the rear end of the wire guide tube 5 is connected to the tubes whose both ends are opened such as a water and air supplying tube 27, thus resulting the wire guide tube 5 opened at its both ends. An extractor leading tube in FIG. 4b can be substituted.

Figure 5:
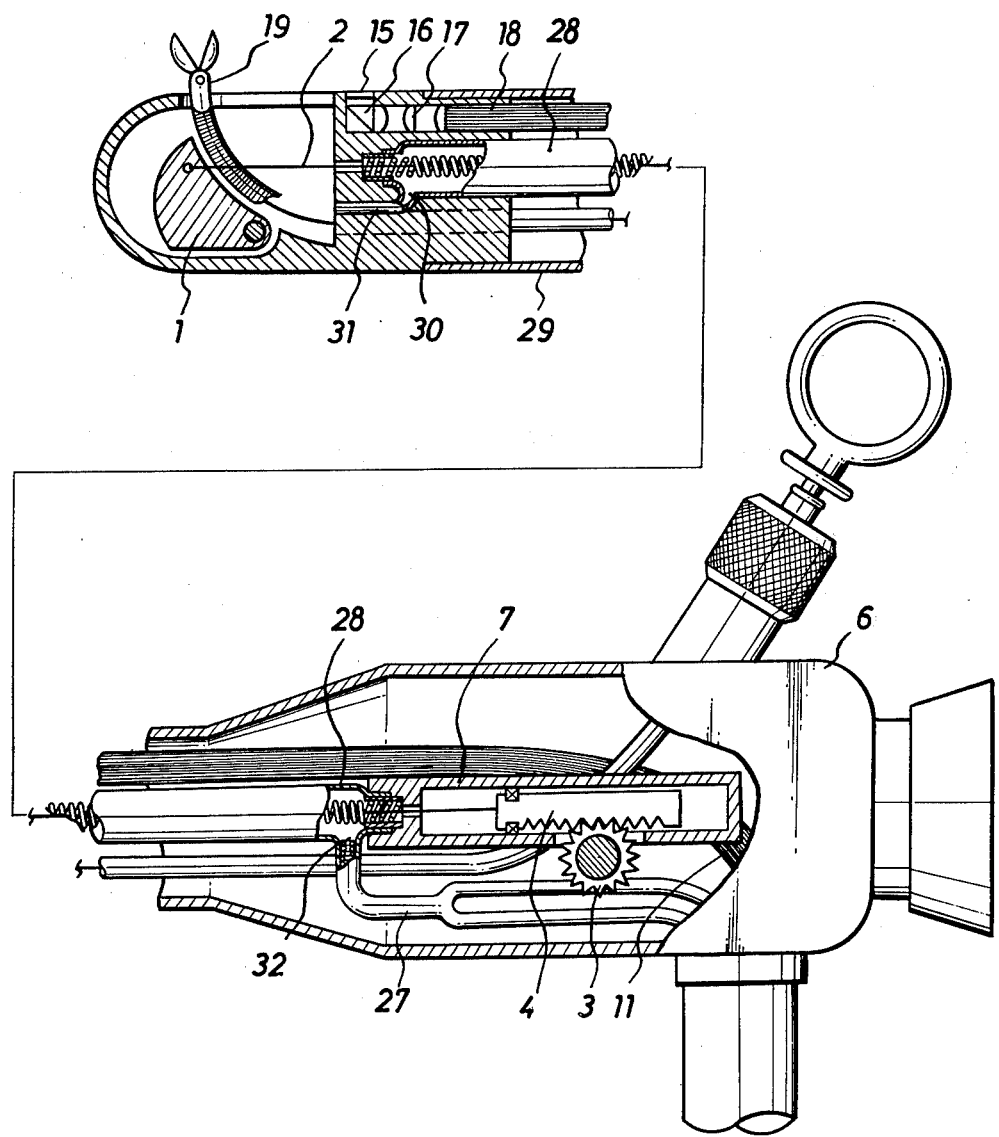
FIG. 5 is a partial sectional view of an embodiment in which a wire guide tube of an extractor operating device is utilized at the same time as a water and air supplying tube whose both ends are opened.

Another embodiment is shown in FIG. 5 in which a common tube 28 is utilized both as a wire guide tube 5 and a water and air supplying tube 27 whose both ends are opened. Said common tube 28 has an opening 30 at the forward end of a flexible sheath 29 of an endoscope, and said opening 30 is connected with a branch 31 which is opened at the forward end of an endoscope. In addition, an opening 32 is provided at the rearward portion in a handle 6, and said opening 32 is connected to a water and air supplying tube 27 whose both ends are opened. By the present embodiment, the both ends of the wire guide tube 5 is opened, and the diameter of the flexible sheath 29 is made smaller by reducing the tubes in the flexible sheath. Accordingly, the flexibility of the flexible sheath 29 is improved.

Figure 6:
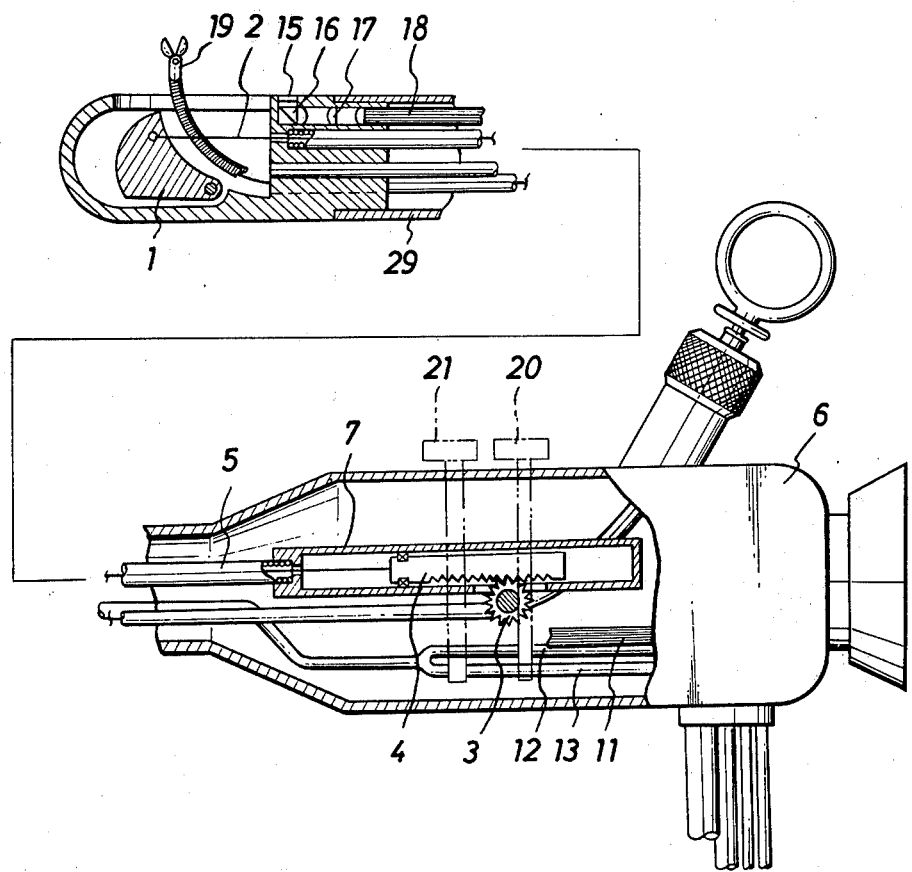
FIGS. 6a, 6b are partial sectional views of embodiments in which piston mechanisms are provided in the hollow portion.
Figure 6:
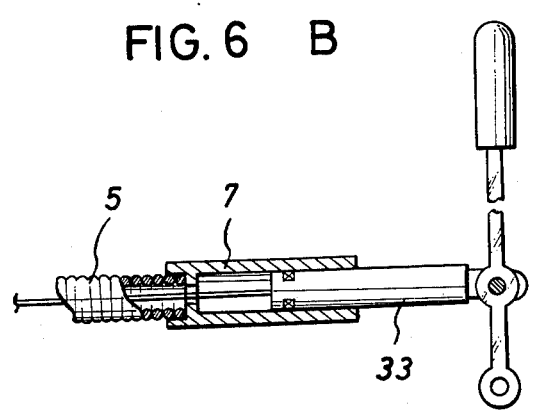

Another embodiment is shown in FIG. 6a in which a packing 8 is equipped, instead of a through tube, around a rack 4 in a hollow portion 7 which is situated at the rear end of the wire guide tube 5. Said rack 4 is slidably supported with the aid of said packing 8, and said rack 4 works as a pump. A cleanser and a disinfectant can be charged or discharged in the wire guide tube at will, thus resulting easy washing and sterilization of said wire guide tube.

Another embodiment is shown in FIG. 6b in which a hollow portion 7 works as a cylinder, and a piston 33 is equipped in said hollow portion 7. The rear end of the operating wire is connected with said piston 33, and said piston 33 is connected to an operating knob ( not shown ) situated outside the handle 6.

We claim:

1. An endoscope having a handle and an operating end interconnected by a sheath, a liquid tube means carried within said sheath for carrying air and liquid, a wire guide tube carried within said sheath housing a guide wire, said guide wire extending from a handle end to a pivoted deflector at said operating end, said guide tube being open at said operating end and being open at said handle end so that said guide tube is open at both its ends, and cleansing means communicating with said open handle end of said wire guide tube enabling cleansing of the interior of said wire guide tube.

2. An endoscope as claimed in claim 1, wherein said cleansing means comprises cleansing tube means connecting said open handle end of said guide wire tube to said handle end of said endoscope.

3. An endoscope as claimed in claim 2, further comprising guide wire movement means located in said handle, said guide wire movement means comprising a rack and pinion, a hollow enclosed housing located in said handle enclosing said rack and pinion, said open handle end of said wire guide tube opening into said hollow housing, an opening formed in said hollow housing to which said cleansing tube is attached.

4. An endoscope as claimed in claim 3, wherein an opening is formed in the rear of said hollow housing, and bypass means connected between the rear and front portions of the hollow housing to carry cleansing fluid and bypass the rack and pinion coupling.

5. An endoscope as claimed in claim 4, wherein said bypass means comprises tube means connected to by-pass the hollow housing, and openings formed at the front and rear of said hollow housing between which said tube means is connected.

6. An endoscope as claimed in claim 2, wherein an opening is formed in the wall of said wire guide tube in the vicinity of the handle end, said cleansing tube being in communication with said opening formed in said wall.

7. An endoscope as claimed in claim 2, wherein said cleansing tube means comprises said liquid tube means, said liquid tube means communicating with the open handle end of said wire guide tube.

8. An endoscope as claimed in claim 1, wherein said cleansing means comprises piston means located in said handle end of said endoscope communicating with said open handle end of said wire guide tube to draw cleansing liquid into and expel said liquid out of said wire guide tube.

9. An endoscope as claimed in claim 8, wherein said piston means comprises a sealed cylinder, said sealed cylinder comprising a hollow housing comprising means to control movement of said wire guide and packing means forming a sealed chamber forming in said hollow housing, said packing being movable by said means to control movement of said guide wire.

* * * * *

REEXAMINATION CERTIFICATE (85th)

United States Patent [19]
Chikama

[11] B1 4,190,041
[45] Certificate Issued May 24, 1983

[54] CLEANING DEVICE FOR WIRE GUIDE TUBE IN AN ENDOSCOPE

[75] Inventor: Toshio Chikama, Tokyo, Japan

[73] Assignee: Machida Endoscope Co., Ltd., Tokyo, Japan

Reexamination Request
 No. 90/000,099, Nov. 3, 1981

Reexamination Certificate for:
 Patent No.: 4,190,041
 Issued: Feb. 26, 1980
 Appl. No.: 832,338
 Filed: Sep. 12, 1977

[51] Int. Cl.³ .................................................. A61B 1/00
[52] U.S. Cl. .......................................... 128/4; 128/6
[58] Field of Search .................................... 128/4, 6
[56] References Cited

U.S. PATENT DOCUMENTS

| | | | |
|---|---|---|---|
| 1,345,406 | 7/1920 | Rimmer | 128/7 |
| 1,627,941 | 5/1927 | Wappler | 128/7 |
| 2,002,595 | 5/1935 | Wappler | 128/7 |
| 2,102,270 | 12/1937 | Hyams | 128/788 X |
| 2,227,727 | 1/1941 | Leggiadro | 128/6 |
| 2,516,494 | 7/1950 | Wallace | 128/5 |
| 3,149,633 | 9/1964 | Zingale | 128/303.15 |
| 3,805,791 | 4/1974 | Sevberth, et al. | 128/303.14 |
| 3,830,225 | 8/1974 | Shinnick | 128/4 X |
| 3,871,365 | 3/1975 | Chikama | 128/5 |
| 3,903,877 | 9/1975 | Terada | 128/6 |

FOREIGN PATENT DOCUMENTS

| | | |
|---|---|---|
| 932574 | 9/1955 | Fed. Rep. of Germany. |
| 47-20990 | 10/1972 | Japan. |
| 52-38987 | 3/1977 | Japan. |
| 548462 | 10/1942 | United Kingdom. |

*Primary Examiner*—S. A. Bratlie

[57] ABSTRACT

The present invention relates to a side view typer or a direct view type endoscope which is used not only for examining the inner portion of stomachs and bowels, but also for cutting out or treating polyps on the wall of stomachs and bowels by an extractor which is inserted through an extractor leading tube of the endoscope. In said endoscope, the rear end portion of a wire guide tube of the extractor operating device is opened or can be opened for washing and sterilization of said wire guide tube.

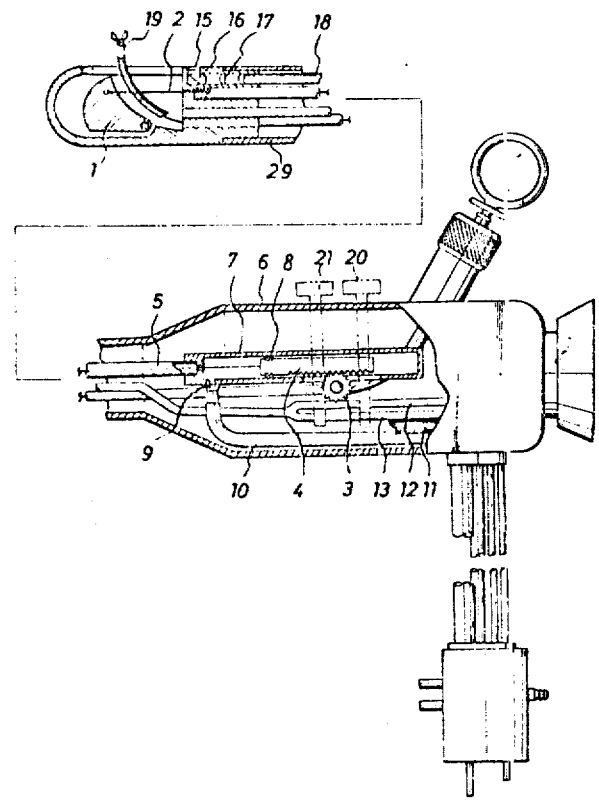

REEXAMINATION CERTIFICATE ISSUED UNDER 35 U.S.C. 307.

THE PATENT IS HEREBY AMENDED AS INDICATED BELOW.

Matter enclosed in heavy brackets appeared in the patent, but has been deleted and is no longer a part of the patent; matter printed in italics indicates additions made to the patent.

AS A RESULT OF REEXAMINATION, IT HAS BEEN DETERMINED THAT:

Claims 1-9, having been finally determined to be unpatentable, are cancelled.

New claim 10 is added and determined to be patentable.

*10. An endoscope having a handle and an operating end interconnected by a sheath, a liquid tube means carried within said sheath for carrying air and liquid, a wire guide tube carried within said sheath housing a guide wire, said guide wire extending from a handle end to a pivoted deflector at said operating end, said wire guide tube being open at said operating end and being open at said handle end so that said guide tube is open at both its ends, an improvement comprising a cleansing tube connecting said open handle end of said wire guide tube to said handle end of said endoscope, further comprising guide wire movement means located in said handle, said guide wire movement means comprising a rack and pinion, a hollow enclosed housing located in said handle enclosing said rack and pinion, said open handle end of said wire guide tube opening into said hollow housing, an opening formed in said hollow housing to which said cleansing tube is attached, an opening formed in the rear of said hollow housing, bypass means connected between the rear and front portions of the hollow housing to carry cleansing fluid and bypass the rack and pinion, said bypass means comprises tube means connected to bypass the hollow housing, and openings formed at the front and rear of said hollow housing between which said tube means is connected.*

\* \* \* \* \*